United States Patent [19]

Cueman et al.

[11] Patent Number: 5,101,366

[45] Date of Patent: Mar. 31, 1992

[54] METHOD FOR CONTROLLING THE MANUFACTURE OF ZIRCONIUM TUBES

[75] Inventors: Michael K. Cueman, Niskayuna, N.Y.; Frederick C. Schoenig, Jr., Wilmington, N.C.; Kurt D. Ellis, Wilmington, N.C.; James D. Landry, Wilmington, N.C.

[73] Assignee: General Electric Company, Schenectady, N.Y.

[21] Appl. No.: 451,665

[22] Filed: Dec. 18, 1989

[51] Int. Cl.$^5$ .............. G06F 15/46; G01N 27/82; G01N 29/04

[52] U.S. Cl. ............ 364/550; 324/238; 324/237; 324/240; 340/680; 364/552; 364/472; 73/622; 29/705; 72/9; 266/99

[58] Field of Search .......... 324/226, 227, 232–234, 324/239–243, 439, 414, 442, 443, 445; 73/622; 72/9, 3, 10, 12; 148/128, 129; 29/705, 723; 266/99, 100; 364/550–552, 480, 481, 472; 340/679, 680

[56] References Cited

U.S. PATENT DOCUMENTS

| | | | |
|---|---|---|---|
| 3,056,081 | 6/1959 | Hochschild | 324/37 |
| 3,732,726 | 5/1973 | Ferber | 73/67.5 R |
| 3,825,822 | 7/1974 | Forster | 324/219 |
| 3,886,793 | 6/1975 | Cramer et al. | 73/167 |
| 4,074,186 | 2/1978 | Flaherty | 324/222 |
| 4,088,953 | 5/1978 | Sarian | 324/232 |
| 4,109,201 | 8/1978 | Pigeon et al. | 324/227 |
| 4,126,491 | 11/1978 | Karlsson | 324/238 X |
| 4,167,878 | 9/1979 | Bottcher et al. | 73/601 |
| 4,335,352 | 6/1982 | Stephen | 324/228 |
| 4,347,622 | 8/1982 | Bernatowicz et al. | 376/245 |
| 4,412,177 | 10/1983 | Petrini et al. | 324/226 |
| 4,414,508 | 11/1983 | Davis et al. | 324/238 |
| 4,449,411 | 5/1984 | Suhr et al. | 73/643 |
| 4,460,869 | 7/1984 | Buser et al. | 324/200 |
| 4,528,856 | 7/1985 | Junker et al. | 73/779 |
| 4,564,810 | 1/1986 | Geithman et al. | 324/230 |
| 4,591,784 | 5/1986 | Kolitsch et al. | 324/208 |
| 4,659,990 | 4/1987 | Torre | 324/238 |
| 4,673,877 | 6/1987 | Sakamoto et al. | 324/225 |
| 4,724,429 | 2/1988 | Millen et al. | 340/679 |
| 4,745,809 | 5/1988 | Collins et al. | 73/661 |
| 4,799,011 | 1/1989 | Muller | 324/240 X |
| 4,808,926 | 2/1989 | Graham et al. | 324/226 |
| 4,856,337 | 8/1989 | Metala et al. | 73/601 |
| 4,862,079 | 8/1989 | Chickering et al. | 324/227 |
| 4,894,848 | 1/1990 | Lambert et al. | 376/261 |
| 4,896,278 | 1/1990 | Grove | 340/679 X |

Primary Examiner—Kenneth A. Wieder
Assistant Examiner—Warren S. Edmonds
Attorney, Agent, or Firm—Paul R. Webb, II; James C. Davis, Jr.

[57] ABSTRACT

A method for operating a computer to control the manufacture process of zirconium tubes in a pilger mill operation, the computer including an electronic memory and being coupled to the pilger mill to receive, as input, data related to the operation of the mill. The method comprising, in one embodiment, the steps of storing in the computer memory respective test signals, each test signal corresponding to a signal obtained by inspecting a tube manufactured by the mill with a respective, known defective operation condition, inspecting a zirconium tube finished by the manufacture process and generating a signal representative of the physical dimensions and material configuration of the tube, comparing the generated representative signal of the zirconium tube with the stored test signals, alerting an operator if the generated representative signal of the zirconium tube correlates to a stored test signal, and identifying the defective operation condition which corresponds to the correlated stored test signal.

3 Claims, 6 Drawing Sheets

OUTPUT VOLTAGES

OUTPUT VOLTAGES

OUTPUT VOLTAGES

OUTPUT VOLTAGES

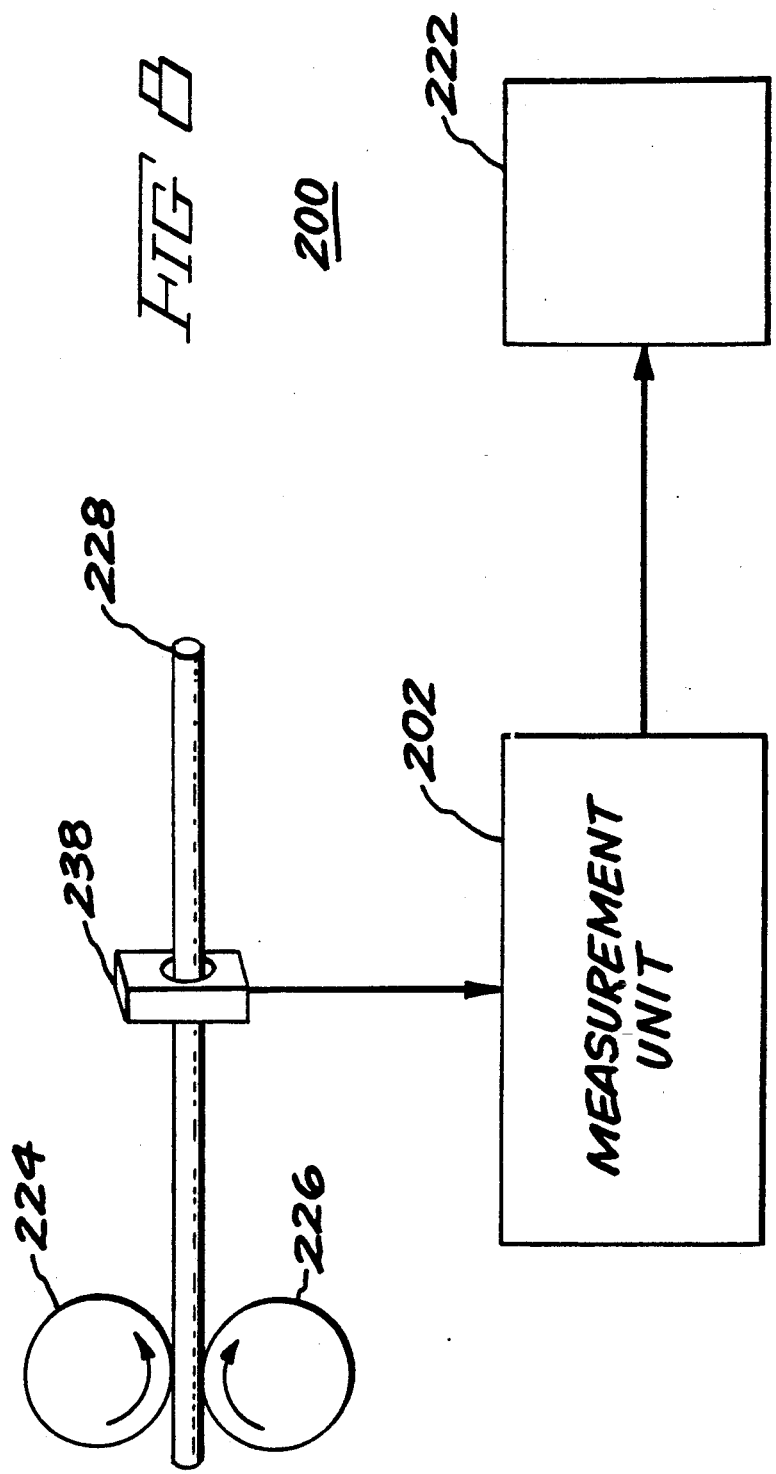

METHOD FOR CONTROLLING THE MANUFACTURE OF ZIRCONIUM TUBES

The present invention relates to a manufacture of zirconium tubes and more specifically, relates to monitoring manufacture of zirconium tubes.

BACKGROUND OF THE INVENTION

The present invention is related to co-pending U.S. patent application Ser. No. 395,108 entitled "Method and Apparatus for Identification of Articles", which is assigned to the present assignee.

Zirconium tubes generally are utilized to contain uranium oxide pellets for nuclear reaction processes. Specifically, uranium pellets are disposed in a zirconium tube, and the tube is sealed at both ends. In operation, the uranium filled zirconium tubes are lowered into water and energy is created due to a chain reaction fissioning of the uranium. The water serves as a necessary moderator of the fission neutrons and as a coolant. The uranium, however, should never be in direct physical contact with the water, otherwise the water becomes contaminated and the reactor must be shut down. The zirconium tubes provide this separation and are the first barrier for the containment of contaminating radiation. Thus, manufacture process control of zirconium tubes is very important. If tube defects can be quickly detected during the manufacturing process, then the cause of the defect can be determined and corrected.

A process for manufacture of zirconium tubes utilized in nuclear reactor processes is commonly referred to as a cold pilger mill process. In this pilger mill process, an ingoing zirconium tube is elongated stepwise over a stationary mandrel. The mandrel is tapered in the direction of rolling. Two grooved rolls, which embrace the tube from above and below, roll over the tube for a predetermined length, sometimes referred to herein as the "pass length".

The rolls receive a reciprocating lateral movement from a saddle in which they are mounted. At the same time, a reciprocating rotary movement is imparted to the rolls by pinions mounted on roll shafts. The reciprocating stroke of the saddle plus rolls is effected by a crank drive.

Grooves in the two rolls form a circular shaped pass which corresponds to the cross section of the ingoing tube. This pass tapers smoothly over a predetermined length of the roll circumference until it reaches the size of the "finished" tube diameter. In this way, the ingoing tube is worked to a desired degree as the rolls carry out their reciprocating movement. The elongation of the ingoing tube to the "finished" tube is effected through reductions in the diameter and wall thickness of the ingoing tube. This is due to the shape of the mandrel and pass which taper from the size of the ingoing tube to the size of the "finished" tube. The length of the tube section reduced per stroke depends on the length of the working pass.

More information regarding the cold pilger process is included in "Machinery and Equipment for the Manufacture of Tubes Using the Cold Pilger Process", Mannesmann Demag Huttentechnik, Zweigniederlassung der Mannesmann Demag AG, Subdivision MEER, Postfach 365, Ohlerkirchweg 66, D-4050 Monchengladbach 1, Fed. Rep. of Germany.

With known processes, once a "finished" tube is formed, the tube is cut and cleaned. Sometimes it also is necessary to straighten the tube. The tube is then inspected for defects. Generally, the process steps of cutting, cleaning, straightening, and inspecting a tube require a time period of at least one week to complete. Therefore, if the pilger mill process is operating in a defective manner, the defect may not be discovered until a week later. This means that a pilger mill may be operating defectively for a substantial period of time before corrective actions are taken. During the time required to detect the defect, many defective tubes may be generated. This causes waste and increases the cost of manufacturing zirconium tubes.

In practice, a pilger mill operator-a human-monitors operation of the mill. Based upon the operator's experience and expertise, the operator adjusts the mill so that higher quality tubes are manufactured. These adjustments may, for example, include the spacing of the rolls, i.e. the roll separation, the speed of roll rotation, the position of the mandrel, and rate of lubrication injection into and between the mandrel and the ingoing tube. Known systems, therefore, are highly dependent upon the experience and expertise of a human operator.

OBJECTS OF THE INVENTION

It is therefore an object of the present invention to provide a method and apparatus for monitoring manufacture of zirconium tubes which overcome these and other shortcomings and disadvantages of the known art.

Another object of the present invention is to provide a method and apparatus for monitoring manufacture of zirconium tubes which provide quick identification of tube defects.

Still another object of the present invention is to provide a method and apparatus for monitoring manufacture of zirconium tubes which reduce waste and costs associated with the zirconium tube manufacture process.

Yet another object of the present invention is to provide a method and apparatus for monitoring manufacture of zirconium tubes which are less dependent than known systems upon the experience and expertise of human operators.

SUMMARY OF THE INVENTION

The present method and apparatus for monitoring manufacture of zirconium tubes includes a detector, such as an eddy current detector or an ultrasound detector, to determine the conductivity or echo characteristics of each tube. The conductivity/echo characteristics of a tube are representative of physical dimensions, i.e. tube geometry, and material configuration of the tube. The detector generally is mounted to the output side of a pilger mill at a location where the "finished" tube exits the mill. It is contemplated that a detector also could be mounted within the mill to monitor tube geometry as the tube is being processed. The detected conductivity and/or echo characteristics are compared, such as by a computer, to ideal characteristics. The ideal characteristics are predetermined and may, for example, be expressed as threshold levels. When the detected conductivity characteristics exceed a predetermined threshold level, the present system alerts the operator that the pilger mill needs to be adjusted. It is contemplated that the present system also could supply the operator with a recommended adjustment and/or could, itself, make the necessary adjustment.

By detecting characteristics of a tube as soon as the tube exits a pilger mill, the present invention provides quick identification of tube defects and reduces waste and costs associated with known zirconium tube manufacture processes. Further, the present monitoring method and apparatus are less dependent upon the experience and expertise of human operators.

BRIEF DESCRIPTION OF THE DRAWINGS

These and other objects of the present invention, together with further features and advantages thereof, will become apparent from the following detailed specification when read together with the accompanying drawings in which:

FIG. 8 is a block diagram of an article identification apparatus in accordance with another embodiment of the present invention.

DETAILED DESCRIPTION OF THE DRAWINGS

Figure 1:
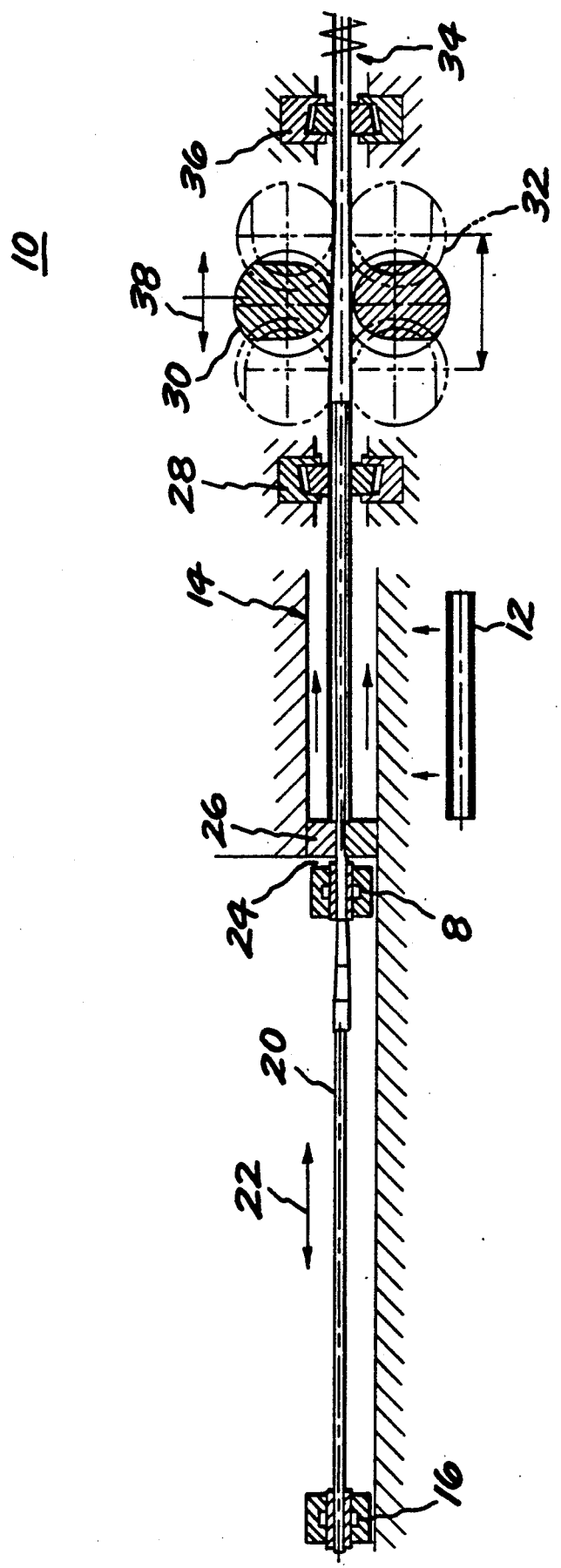
FIG. 1 is a schematic illustration of an intermittent side loader cold pilger mill.

FIG. 1 is a schematic illustration of an intermittent side loader cold pilger mill 10. The present invention is not limited to use with any specific type of process for manufacture of zirconium tubes and the pilger mill illustrated in FIG. 1 is shown for explanatory purposes only. Further, it should be understood that many other types of pilger mill processes are known, commercially available, and could be utilized with the present invention.

Cold pilger mill 10 is referred to as an intermittent side loader because an ingoing tube 12 is inserted into mill 10 at an intermittent and side location 14. Other types of known cold pilger mills include intermittent rear loader mills wherein a zirconium tube is loaded from a rear section of the mill and at an intermittent location. Mill 10 includes movable thrust blocks 16 and 18. A thrust rod 20 is disposed between and connected to blocks 16 and 18. As indicated by arrow 22, the thrust block and rod move laterally relative to other portions of mill 10. Thrust block 18 also supports a mandrel rod 24 which passes through a feed carriage 26. Mandrel rod 24 is inserted into ingoing tube 12. The assembly of the mandrel rod and ingoing tube pass through an entry chuck 28 and between spaced and opposed rolls 30 and 32. Rolls 30 and 32 are supported in a saddle (not shown). A "finish" portion 34 of rod 12 passes through an exit turning chuck 36.

In operation, ingoing tube 12 is inserted into the mill at location 14. Movable thrust blocks 16 and 18 are moved laterally relative to the remaining portions of the mill thereby causing a mandrel rod to be inserted into and come in contact with ingoing tube 12. The assembly of the mandrel rod and ingoing tube are passed through entry chuck 28 and between spaced rolls 30 and 32. Rolls 30 and 32 rotate and undergo a reciprocating lateral movement as indicated by arrow 38. Grooves (not shown) in the rolls form a circular shaped pass which correspond to the cross section of the ingoing tube. This pass tapers smoothly over a predetermined length of the roll circumference until it reaches the size of the finished tube diameter. In this way, the ingoing tube is worked to the desired degree as the rolls carry out their reciprocating movement. Elongation of the ingoing tube to a finish tube is affected through reductions in the diameter wall thickness. This is due to the shape of the mandrel and pass, which tapers from the size of the ingoing tube to the size of a finished tube.

Figure 2:
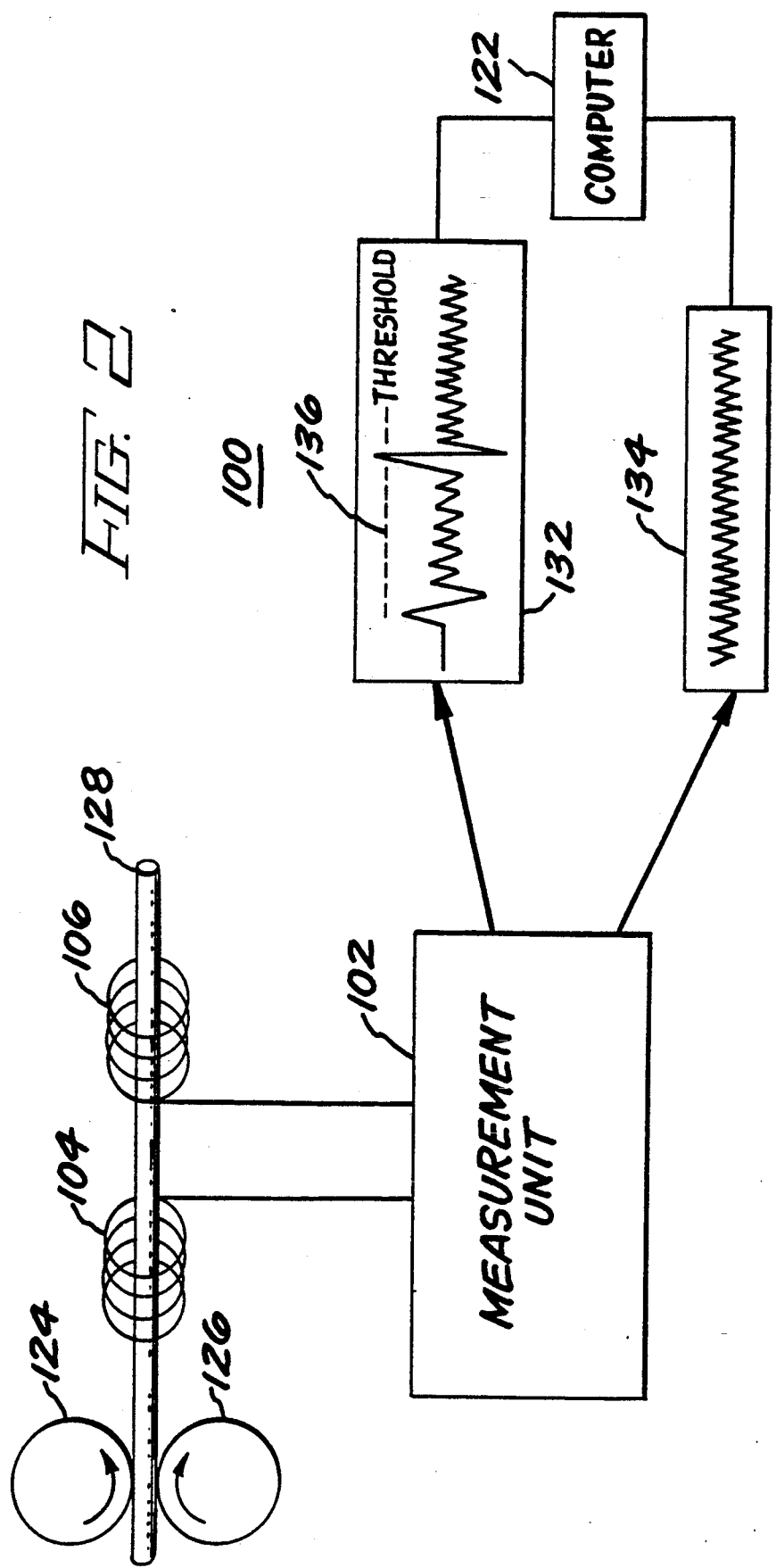
FIG. 2 is a block diagram of a monitoring apparatus in accordance with the preferred embodiment of the present invention.

FIG. 2 illustrates in block diagram the preferred embodiment of a section of a monitoring apparatus 100 in accordance with the present invention. Apparatus 100 includes a measurement unit 102 having sensor coils 104 and 106. Each sensor coil includes a longitudinal axis and an interior space which extends coaxially along the longitudinal axis. The interior space has a diameter such that an article can be passed therethrough along the longitudinal axis of the coil as hereinafter explained.

Figure 3:
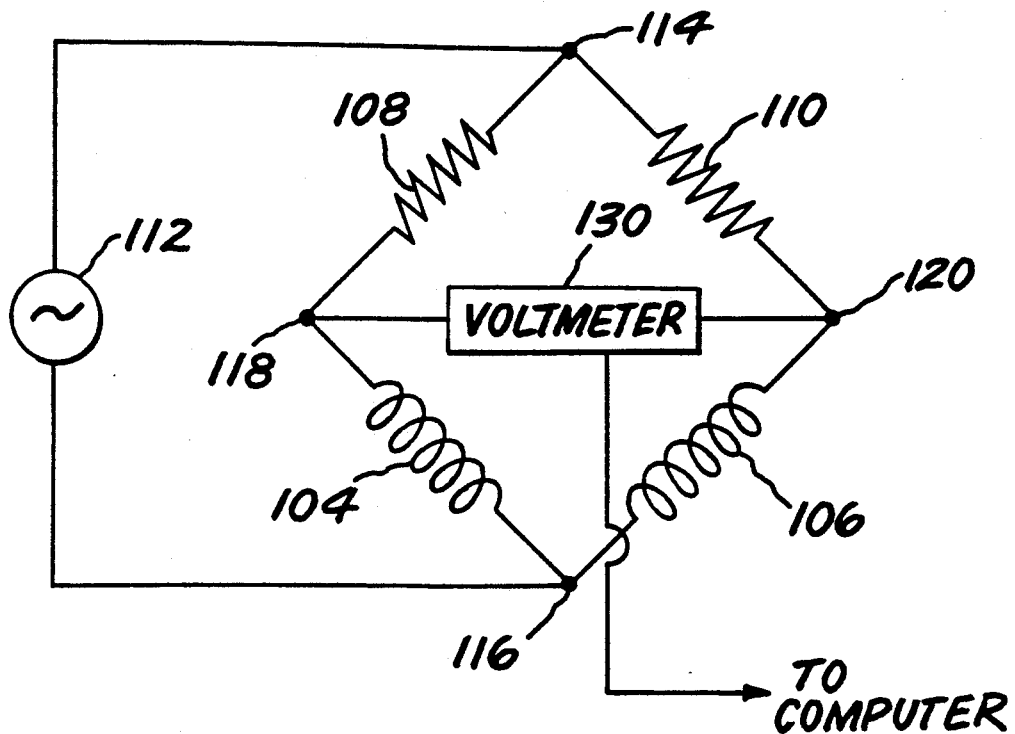
FIG. 3 is a circuit diagram of a bridge circuit which forms part of the monitoring apparatus of FIG. 1.

As best shown in FIG. 3, measurement unit 102 further includes resistors 108 and 110. The resistors and the sensor coils are connected to form a bridge circuit. The resistors preferable have a substantially equal resistance and the coils preferably have a substantially equal impedance. The measurement unit further includes a drive source 112 which generates an AC drive signal supplied to the bridge circuit at input nodes 114 and 116. Output nodes 118 and 120 of the bridge circuit are connected to a voltage measuring means shown as a volt meter. The output of the volt meter is connected to a computer 122 for recording, storing and comparing the signals output by the bridge circuit as hereinafter explained. The computer may be a conventional personal computer (PC) and generally should include an analog-to-digital converter for converting the analog signal from the measuring unit to a digital signal to be stored in the computer. Feedrolls 124 and 126, as shown in FIG. 2, are utilized to feed a zirconium tube 128 to the measurement unit. The feedrolls are aligned with sensor coils 104 and 106 so that zirconium tube 128 can be fed through the interior space of the coils.

Before operation, drive source 112 is activated and supplies the AC drive signal to the bridge circuit. Sensor coils 104 and 106 should be remote from any conductor at this time. The output signals present on output nodes 118 and 120 then are compared with each other by means such as volt meter 130 and the magnitudes of impedance of the components which comprise the bridge circuit are adjusted so that the output signals are substantially equal. This process generally is referred to as "balancing" the bridge circuit. If the resistors have an equal resistance and the coils have an equal impedance, then the bridge circuit output signals should be substantially equal without adjustment when the sensor coils are remote from a conductor.

In operation, after zirconium tube 128 is passed through exit turning chuck 36, tube 128 is inserted between feedrolls 124 and 126. The feedrolls direct the zirconium tube to pass through the openings formed by sensor coils 104 and 106 and constrain it to reduce lateral vibrations. As is well-known, transmitting the AC signal through the sensor coils causes each coil to generate an electromagnetic field. As the zirconium tube passes through each coil, eddy currents are induced in the zirconium tube by the respective magnetic field. The magnetic flux of the eddy currents interacts with the magnetic field of the sensor coil, and this interaction causes impedance changes to occur in the sensor coil.

The impedance changes which sensor coils 104 and 106 undergo causes the bridge circuit to become unbalanced therefore causing changes in the output signals at the output terminals of the bridge circuit. The output signals, i.e., the in-phase and the out-of-phase signals, from the bridge circuit, as illustrated in blocks 132 (the in-phase signal and 134 the out-of-phase signal of FIG. 2, are transmitted to the computer and these signals are recorded and stored in the computer's archival memory.

The output signals of the measuring unit are unique identifiers of the individual tubes because the conductivity and small changes in physical dimensions form patterns which vary from tube to tube. The eddy currents induced in the tube at each specific location are functions of both the local conductivity and dimensions at the location. Although the material configuration, in general, is constant, the configuration varies slightly along the length of each tube. The conductivity characteristics may have similar small variations along the length of the tube.

As illustrated in block 132 of FIG. 2, the eddy current measurements may also be utilized to inspect each tube. Specifically, small discontinuities or other deformations in the tube will cause discontinuities or greater than normal changes in the eddy currents. These discontinuities and/or changes in the eddy current affect the output signal of the measurement unit. To detect these changes in the output signal, a threshold signal level 136 is determined, for example by experiment. Then during operation, if the output signal of the measurement unit exceeds the threshold level, the computer alarms the operator of the possible existence of a defect.

More specifically, a flaw in a zirconium tube generally appears as a single spike-like discontinuity in a signal baseline, such as shown in FIG. 2. By triggering an alarm whenever a pre-determined threshold is exceeded, a system user can be alerted to the fact that a defective tube has been detected. To eliminate DC drift in the baseline signal, it may be preferred to bandpass filter the signal from measurement unit 102. Another option is to convert the signal from unit 102 into a digital signal, and then correlate the digitized spike-like discontinuity with a pre-determined, digitized flaw characteristic signal. An alarm would be activated when the correlation becomes sufficiently strong enough to identify a flaw.

Further, in addition to identifying a zirconium tube having a flaw thereby at least notifying an operator that some adjustment may be necessary, the present invention may be utilized to monitor tube manufacture. Specifically, a series of tests could be performed wherein the pilger mill process is set-up to have a variety of known defects. For example, in one series of tests, the spacing of the rolls may be defective. In another series of tests, the speed of roll rotation may be defective.

The signals generated by the measurement unit during each test would be stored in the system memory along with the type of known defect. Every conceivable defect and combination of defects in the pilger mill process could be utilized to generate the test data.

During manufacture of the tubes, the signal generated by the measurement unit would be compared with each test measurement, or some signal representative of the result of each series of test measurements. If a strong correlation between a tube generated signal and any test measurement signal occurs, then the system would alert the operator of the defect and also provide a recommended adjustment. For example, if a tube generated signal sufficiently corresponds to the test signal measurement generated when roll separation was defective, the system would recommend that roll separation be adjusted.

Depending upon the number and variety of test measurements performed, the system recommendation may even provide the magnitude of the recommended adjustment. This recommendation may be embodied in many forms, including utilizing artificial intelligence techniques such as fuzzy logic and reasoning with uncertainty. Further, rather than requiring a human operator to make the adjustment, the system could be coupled to electrically controlled mechanisms which make an adjustment to the process upon receipt of an electrical control signal.

FIGS. 4-7 illustrate output signals of measuring unit 102 as recorded by a strip chart device for four different tubes. In FIG. 4A, the record shown corresponds with the in-phase signal from the volt meter, i.e., the signal which is in-phase with the AC drive signal, and the record shown in FIG. 4B corresponds with the out-of-phase signal from the volt meter.

Figure 5A:
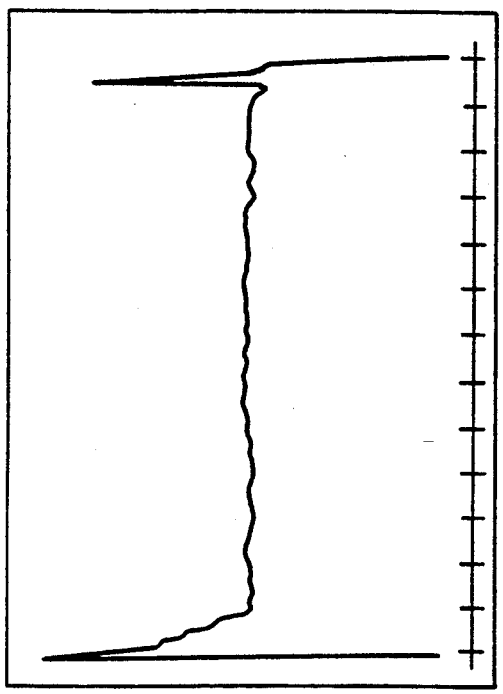
FIGS. 4A, 4B, 5A, 5B, 6A, 6B, 7A, and 7B are recordings of signals made by the monitoring apparatus of FIG. 1 for different tubes.
Figure 5B:
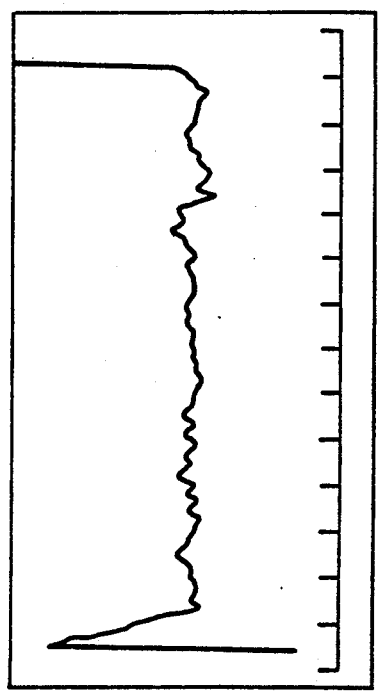
Figure 4A:
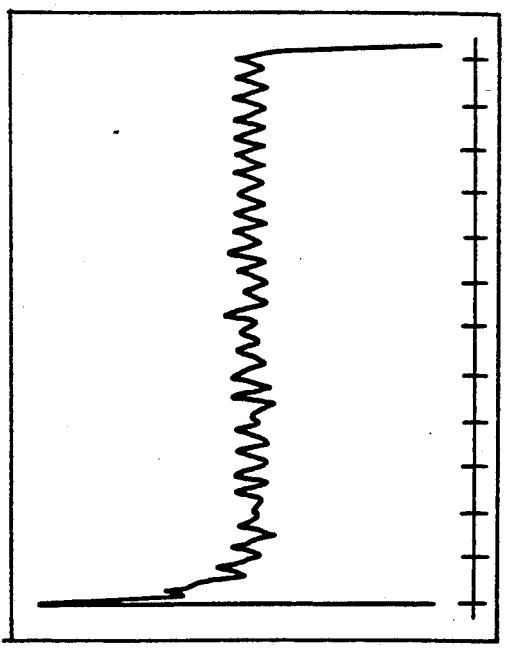
Figure 4B:
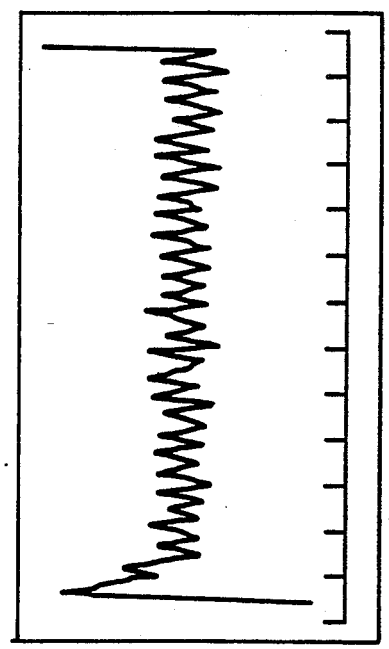
Figure 7A:
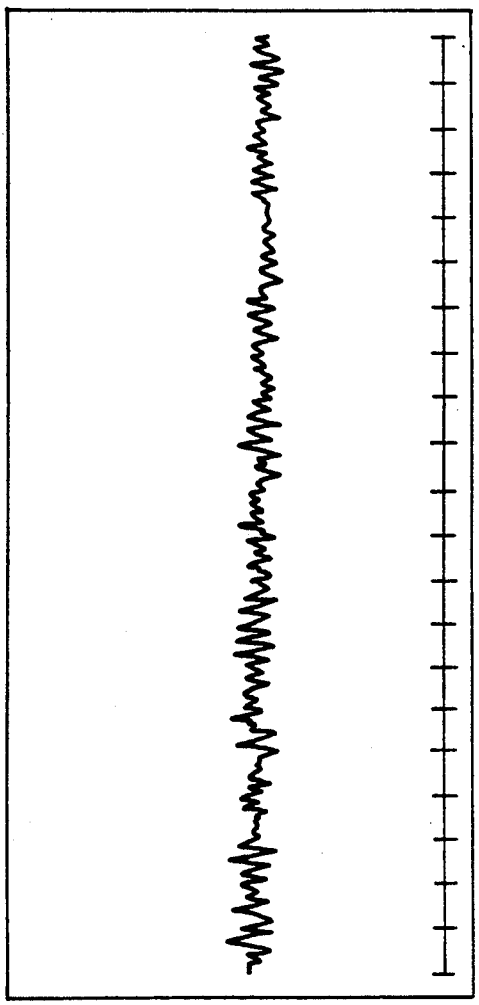
Figure 7B:
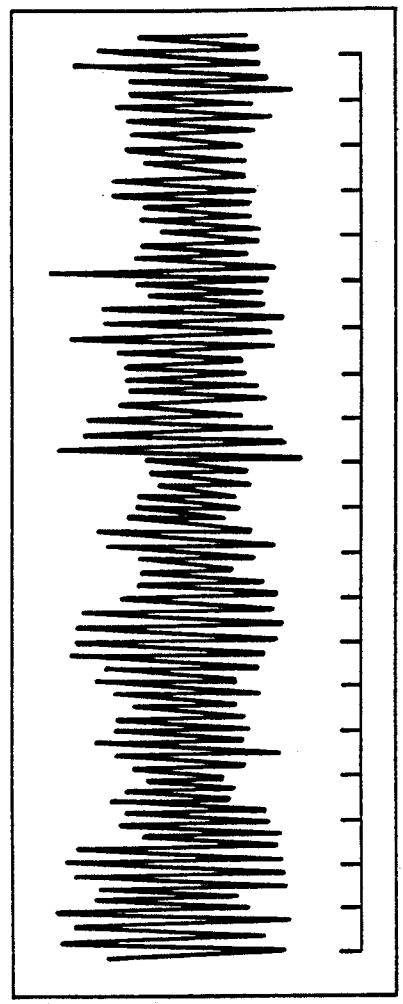
Figure 6A:
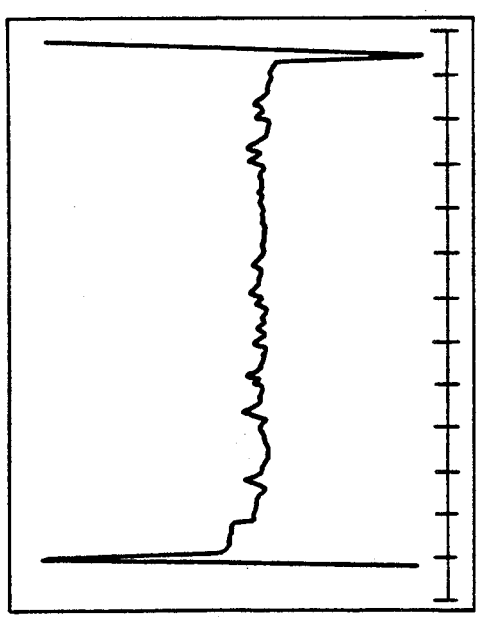
Figure 6B:
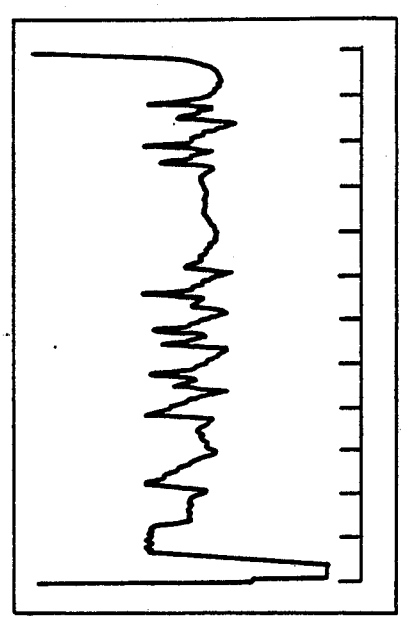

FIGS. 5A-B show the in-phase and out-of-phase signals, respectively, of the measuring unit for another zirconium tube. FIGS. 6A-B show the in-phase and out-of-phase signals, respectively, of the measuring unit for still another zirconium tube, and FIGS. 7A-B show the in-phase and out-of-phase signals, respectively, of the measuring unit for still yet another zirconium tube. FIGS. 4-7 are shown to illustrate that each zirconium tube will cause the measurement unit to develop unique output signals for each tube.

FIG. 8 illustrates, in block diagram, another monitoring apparatus 200 in accordance with the present invention. Components of apparatus 200 have the same last two digits as the corresponding components, if any, of apparatus 100 shown in FIG. 2. Apparatus 200 utilizes an ultrasound sensor 238 for developing characteristic signals utilized to identify each individual tube. The sensor is connected to a measurement unit 202 which is connected to computer 222.

In operation, zirconium tube 228 is passed through sensor 238 by feedrolls 224 and 226. The output of the sensor is transmitted to the measurement unit which develops the characteristic signals. As is well-known, the signal output by the ultrasound sensor and measurement unit will be related to the echo characteristics of the tube being measured. Since each individual tube has unique echo characteristics, the output signal from the measurement unit will be unique for each individual tube. These signals can be stored for later use e.g., for comparison with each test measurement as hereinbefore described.

Figure 9:
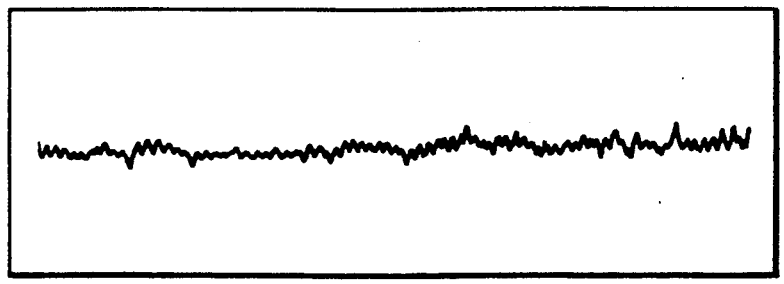
FIGS. 9-10 are recordings of measurement signals made by the monitoring apparatus of FIG. 8 for different tubes.
Figure 10:
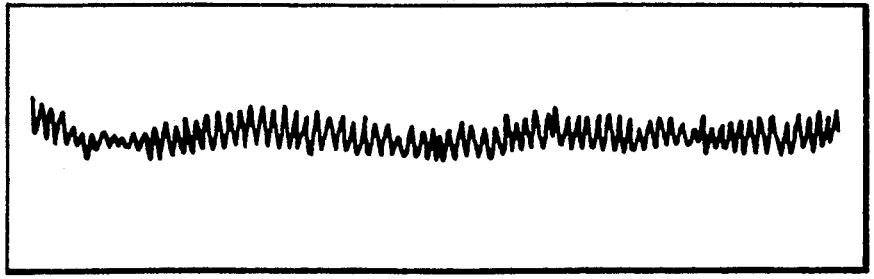

FIGS. 9 and 10 illustrate output signals of measurement unit 202 for different tubes. As is readily apparent from these recordings, each tube causes the measurement unit to develop unique characteristic signals.

The present monitoring apparatus is not limited to eddy current or ultrasound measurements. For example, eddy current and ultrasound measurements both could be utilized to measure the characteristics of each tube, and the tube identified by the eddy current measurement comparisons could be compared to the tube identified by ultrasound measurement comparisons. If both measurements identify the same tube, then one type of measurement could be said to have verified the other type of measurement. Further, in a combined eddy current/ultrasound measurement system, dimensional information obtained from ultrasound measurements could be utilized to sort dimensional/conductivity information obtained from eddy current measurements. Many other types of measurement are contemplated and are within the scope of the present invention.

While specific embodiments have been illustrated and described herein, it will be obvious that numerous modifications, changes, variations, substitutions and equivalents, in whole or in part, will now occur to those skilled in the art without departing from the spirit and scope contemplated by the invention. Accordingly, it is intended that the invention herein be limited only by the scope of the appended claims.

What is claimed is:

1. A method for monitoring the manufacture process of zirconium tubes in a pilger mill operation, a computer including an electronic memory and being coupled to the pilger mill to receive, as input, data related to the operation of the mill, said method comprising the steps of:

storing in the computer memory respective test signals, each test signal being representative of the physical dimensions and material configuration of a test zirconium tube, each test zirconium tube having been manufactured by the mill with a respective, known defective operation condition of the mill;

inspecting a zirconium tube to be actually used and finished by the manufacture process and generating a signal representative of the physical dimensions and material configuration of the tube;

comparing the generated representative signal of the zirconium tube with the stored test signals;

alerting an operator if the generated representative signal of the zirconium tube correlates to a stored test signal; and identifying the defective operation condition of the mill which corresponds to the correlated stored test signal.

2. A method in accordance with claim 1 wherein generating a representative signal comprises the step of detecting conduction characteristics of the tube.

3. A method in accordance with claim 1 wherein generating a representative signal comprises the step of detecting echo characteristics of the tube.

* * * * *